US012778990B2

(12) United States Patent
Takeuchi et al.

(10) Patent No.: US 12,778,990 B2

(45) Date of Patent: Nov. 3, 2026

(54) COMPOSITION FOR BABIES AND INFANTS FOR IMPROVING MEMORY ABILITY IN CHILDHOOD

(71) Applicant: MORINAGA MILK INDUSTRY CO., LTD., Tokyo (JP)

(72) Inventors: Takashi Takeuchi, Tottori (JP); Akari Hiraku, Kanagawa (JP); Noriyuki Iwabuchi, Kanagawa (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 339 days.

(21) Appl. No.: 17/633,386

(22) PCT Filed: Aug. 7, 2020

(86) PCT No.: PCT/JP2020/030425

§ 371 (c)(1),
(2) Date: Feb. 7, 2022

(87) PCT Pub. No.: WO2021/025154

PCT Pub. Date: Feb. 11, 2021

(65) Prior Publication Data

US 2022/0288138 A1 Sep. 15, 2022

(30) Foreign Application Priority Data

Aug. 8, 2019 (JP) ................................ 2019-146115

(51) Int. Cl.

*A61K 35/745* (2015.01)
*A61K 35/00* (2006.01)
*A61P 25/28* (2006.01)

(52) U.S. Cl.

CPC ............ *A61K 35/745* (2013.01); *A61P 25/28* (2018.01); *A61K 2035/115* (2013.01)

(58) Field of Classification Search

None
See application file for complete search history.

(56) References Cited

U.S. PATENT DOCUMENTS 6,284,243 B1 9/2001 Masuyama et al.
2011/0280837 A1 11/2011 Bergonzelli et al.
(Continued)

FOREIGN PATENT DOCUMENTS

CA 3167205 A1 * 7/2012 ............ A23L 33/40
CN 108541951 A 9/2018
(Continued)

OTHER PUBLICATIONS

Capizzano et al. The Hours That Children Under Five Spend in Child Care: Variation Across States. New Federalism. Series B, No. B-8, Mar. 2000, 11 pages. Retrieved from https://www.urban.org/sites/default/files/publication/62106/309439-The-Hours-That-Children-Under-Five-Spend-in-Child-Care.PDF on Jan. 13, 2026.*
(Continued)

*Primary Examiner* — Oluwatosin A Ogunbiyi

(74) *Attorney, Agent, or Firm* — Cermak & McGowan LLP; Shelly Guest Cermak

(57) ABSTRACT

A problem of the invention is to provide a technique for improving memory ability in later childhood, and the problem is solved by a composition for an infant and/or child for improving memory ability in later childhood, wherein the composition contains *Bifidobacterium longum* subsp. *infantis* as an active ingredient.

16 Claims, 1 Drawing Sheet

(56) References Cited

U.S. PATENT DOCUMENTS

| | | | |
|---|---|---|---|
| 2017/0354696 | A1 | 12/2017 | Albrecht et al. |
| 2019/0134114 | A1 | 5/2019 | Kusuda et al. |

FOREIGN PATENT DOCUMENTS

| | | | | |
|---|---|---|---|---|
| JP | 9-23848 | A | 1/1997 | |
| JP | 2011-517568 | A | 6/2011 | |
| JP | 2015-224193 | A | 12/2015 | |
| WO | WO-2012062782 | A1 * | 5/2012 | ........... A61K 35/745 |
| WO | WO2014/070016 | A2 | 5/2014 | |
| WO | WO-2015034984 | A1 * | 3/2015 | ............. A23L 33/12 |
| WO | WO2017/130859 | A1 | 8/2017 | |
| WO | WO2017/179602 | A1 | 10/2017 | |
| WO | WO-2018180728 | A1 * | 10/2018 | ........... A23L 33/135 |
| WO | WO2018/215573 | A1 | 11/2018 | |

OTHER PUBLICATIONS

Cazzola et al. Ther Adv Respir Dis (2010) 4(5) 271-278.*
Extended European Search Report issued in corresponding EP application No. 20849445.0; dated Jul. 27, 2023.
Database GNPD Mintel; Vanilla Flavored Food Supplement; (2018) Database Accession No. 5544057, XPO93062940, downloaded from the internet on Sep. 23, 2023.
Inoue T. et al., Effect of combined bifidobacteria supplementation and resistance training on cognitive function, body composition and bowel habits of healthy elderly subjects; Beneficial Microbes, vol. 9, No. 6, (2018); pp. 843-853.
International Search Report for PCT Patent App. No. PCT/JP2020/030425 (Oct. 13, 2020).

* cited by examiner

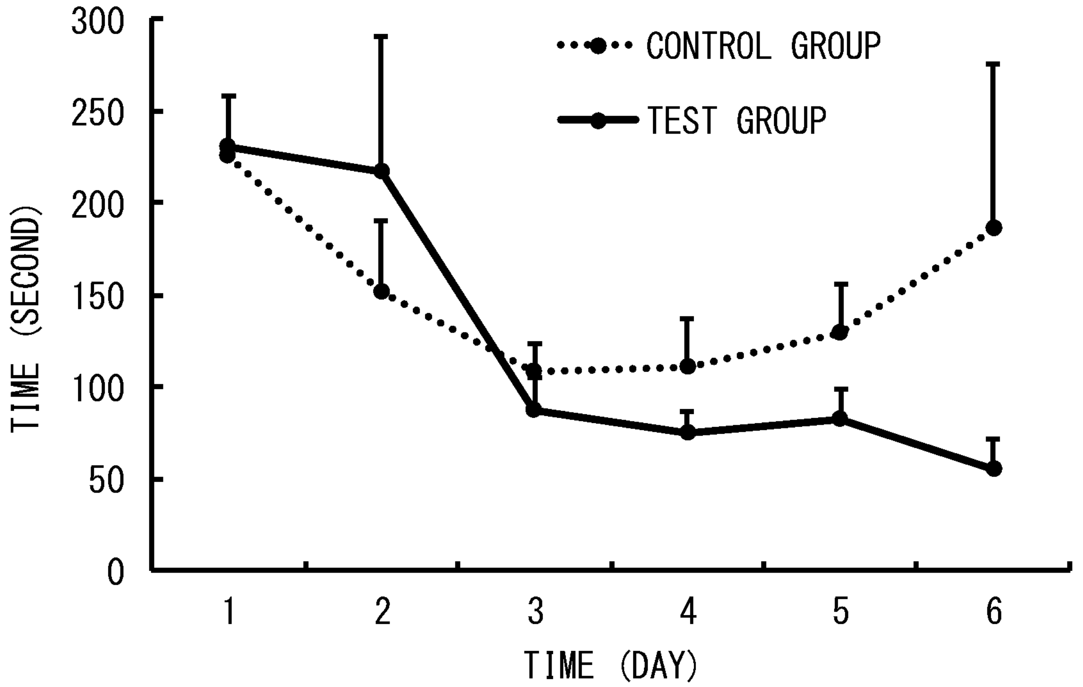
300
250
200
150
100
50
0
TIME (SECOND)
CONTROL GROUP
TEST GROUP
1
2
3
4
5
6
TIME (DAY)

COMPOSITION FOR BABIES AND INFANTS FOR IMPROVING MEMORY ABILITY IN CHILDHOOD

This application is a U.S. national phase filing of, and claims priority under 35 U.S.C. § 371 to, International Application No. PCT/JP2020/030425, filed Aug. 7, 2020, and claims priority therethrough under 35 U.S.C. § 119 to Japanese Patent Application No. 2019-146115, filed Aug. 8, 2019, the entireties of which are incorporated by reference herein.

TECHNICAL FIELD

The present invention relates to a composition for an infant and/or child for improving memory ability in later childhood containing *Bifidobacterium longum* subsp. *infantis* as an active ingredient.

BACKGROUND ART

One of the abilities which develop in later childhood is memory ability. Various techniques which support the improvement of memory of children in later childhood have been developed so far. For example, as ingredients which are effective for enhancing memory, eicosapentaenoic acid, docosahexaenoic acid and the like have been found, and a functional food or drink having memory-enhancing ability containing humulone or the like contained in hop extracts as an active ingredient and the like have been developed (Patent Document 1).

*Bifidobacterium* bacteria are known as good germs which are the most abundant in human intestines and are widely utilized as kinds of probiotics. Some of *Bifidobacterium* bacteria exhibit effects related to memory.

For example, it is reported that an edible composition containing *Bifidobacterium longum* ATCC BAA-999 increases the expression of brain-derived neurotrophic factor (BDNF) in the hippocampus, which is known to be involved in memory (Patent Document 2). In addition, a composition for improving brain function for neonates containing *Bifidobacterium bifidum* NITE BP-31 as an active ingredient has been developed. Specifically, it has been confirmed that the developmental quotients of certain neonates evaluated by the Kyoto Scale of Psychological Development 2001 increase significantly (Patent Document 3).

However, it has not been reported that *Bifidobacterium longum* subsp. *infantis* is effective for improving the memory ability in later childhood in subjects who have taken or have been administered *Bifidobacterium longum* subsp. *infantis* in their infant and/or child period.

CITATION LIST

Patent Literature

Patent Document 1: JP2015-224193A
Patent Document 2: JP2011-517568A
Patent Document 3: WO2017/179602

SUMMARY OF INVENTION

Technical Problem

A problem of the invention is to provide a technique for improving memory ability in later childhood.

Solution to Problem

The present inventors have found that *Bifidobacterium longum* subsp. *infantis* is effective for improving the memory ability in later childhood in subjects who have taken or have been administered *Bifidobacterium longum* subsp. *infantis* in their infant and/or child period, and the inventors have thus completed the invention.

That is, the invention provides a composition for an infant and/or child for improving the memory ability in later childhood, wherein the composition contains *Bifidobacterium longum* subsp. *infantis* as an active ingredient.

In a preferable embodiment of the composition, the *Bifidobacterium longum* subsp. *infantis* is *Bifidobacterium longum* subsp. *infantis* NITE BP-02623.

In a preferable embodiment of the composition, the memory ability is working memory ability.

In a preferable embodiment, the composition is a food or drink composition.

Advantageous Effects of Invention

The composition of the invention can improve the memory ability in later childhood in subjects who have taken or have been administered *Bifidobacterium longum* subsp. *infantis* in their infant and/or child period.

BRIEF DESCRIPTION OF DRAWINGS

FIGURE shows a graph showing the results of Example 1 of the invention.

DESCRIPTION OF EMBODIMENTS

The invention is explained in detail below.

In this specification, the composition for an infant and/or child for improving memory ability in later childhood, wherein the composition contains *Bifidobacterium longum* subsp. *infantis* as an active ingredient is sometimes referred to as "the composition of the invention". The composition of the invention is a concept including a mixture, and the components may be homogeneous or heterogeneous.

In this specification, *Bifidobacterium longum* subsp. *infantis* is sometimes referred to as "the bacterium of the invention".

The composition of the invention contains *Bifidobacterium longum* subsp. *infantis* as an active ingredient. The bacterium is a *Bifidobacterium* bacterium and is a Gram-positive obligatory anaerobic bacillus.

In this regard, *Bifidobacterium longum* subsp. *infantis* is sometimes simply referred to as *Bifidobacterium infantis*.

Specific examples of *Bifidobacterium longum* subsp. *infantis* include *Bifidobacterium longum* subsp. *infantis* NITE BP-02623, *Bifidobacterium longum* subsp. *infantis* Bi-26 (DuPont Danisco), *Bifidobacterium longum* subsp. *infantis* R0033 (Lallemand), *Bifidobacterium longum* subsp. *infantis* CECT7210 (Biopolis), *Bifidobacterium longum* subsp. *infantis* CECT2710 (Biopolis), and *Bifidobacterium longum* subsp. *infantis* EVC001 (Evolve BioSystems).

The bacterium to which the accession number of NITE BP-02623 was given was deposited as an international deposit under the Budapest Treaty on Jan. 26, 2018 to NITE Patent Microorganisms Depositary, National Institute of Technology and Evaluation (Room 122, 2-5-8 Kazusakamatari, Kisarazu-shi, Chiba 292-0818) and given the accession number of NITE BP-02623. The bacterium is the same bacterium as *Bifidobacterium longum* subsp. *infantis* M-63.

*Bifidobacterium longum* subsp. *infantis* NITE BP-02623 is not limited to the deposited bacterium and may be a bacterium which is substantially equivalent to the deposited bacterium. A bacterium which is substantially equivalent to the deposited bacterium is as follows: the bacterium is a bacterium classified as *Bifidobacterium longum* subsp. *infantis*; the bacterium can improve the memory ability in later childhood of a subject who has taken or has been administered the bacterium in the infant and/or child period; the nucleotide sequence of 16SrRNA gene thereof has a homology of preferably 98% or higher, further preferably 99% or higher, more preferably 100% to the nucleotide sequence of 16SrRNA gene of the deposited bacterium; and the bacterium is preferably a bacterium having the same mycological properties as those of the deposited bacterium. *Bifidobacterium longum* subsp. *infantis* NITE BP-02623 also includes a mutant and a gene recombinant strain derived from the bacterium.

The same applies to the other bacteria above.

In the invention, one strain of *Bifidobacterium longum* subsp. *infantis* may be used, and two or more strains thereof may also be used.

*Bifidobacterium longum* subsp. *infantis* can be easily grown by culturing the bacterium. The method for cultivation is not particularly limited as long as the bacterium can grow, and a method which is generally used for culturing *Bifidobacterium* bacteria (*bifidobacteria*) can be used with appropriate modification when necessary. For example, the culture temperature may be 25 to 50° C. and is preferably 30 to 40° C. Moreover, cultivation is conducted preferably under anaerobic conditions, and for example, cultivation can be conducted while flowing an anaerobic gas such as carbon dioxide. Furthermore, cultivation may be conducted under microaerophilic conditions such as static liquid culture.

The medium used for cultivation is not particularly limited, and a medium which is generally used for culturing a *Bifidobacterium* bacterium can be used with appropriate modification when necessary. That is, as a carbon source, for example, saccharides such as galactose, glucose, fructose, mannose, cellobiose, maltose, lactose, sucrose, trehalose, starch, starch hydrolysate, and molasses can be used depending on the assimilation properties. As a nitrogen source, for example, ammonia and ammonium salts and nitrates such as ammonium sulfate, ammonium chloride and ammonium nitrate can be used. Moreover, as an inorganic salt, for example, sodium chloride, potassium chloride, potassium phosphate, magnesium sulfate, calcium chloride, calcium nitrate, manganese chloride, ferrous sulfate, and the like can be used. Furthermore, organic components such as peptone, soybean powder, a defatted soybean cake, meat extract, and yeast extract may also be used. In addition, as a modified medium, for example, MRS medium can be preferably used.

A culture obtained after culturing the bacterium of the invention may be used directly or used after dilution or concentration, or bacterial cells collected from a culture may also be used. Moreover, as long as the effects of the invention are not impaired, various additional operations such as heating and freeze-drying can be conducted after cultivation. The bacterium of the invention may be living cells or dead cells. The dead cells are dead cells which have been sterilized by heating or the like.

The bacterium of the invention has an action of improving the memory ability in later childhood of a subject who has taken or has been administered the bacterium in the infant and/or child period. Therefore, the bacterium of the invention can be used as an active ingredient in a composition for an infant and/or child for improving the memory ability in later childhood.

The subject which takes or is administered the composition of the invention is a human or a mammal other than human. Examples of the mammal other than human include cattle, goat, sheep, pig, monkey, dog, cat, rat, mouse, hamster, guinea pig, and the like.

When the subject is a human, the subject who takes or is administered the composition of the invention may experience separation from the mother (namely maternal separation) in the infant and/or child period but does not have to experience the separation. The maternal separation is, for example, separation of a mother and offspring in the daily lives although the separation of the mother and the offspring is for a short time. For example, a mother and offspring who live together for most of a day are separated from each other because the offspring is left at a day-care center or the like for some hours of a day. The period for the separation of the mother and the offspring is, for example, three hours or longer and 12 hours or shorter per day.

When the subject is a mammal other than human, the subject which takes or is administered the composition of the invention may experience separation from the keeper in the infant and/or child period but does not have to experience the separation.

The composition of the invention is taken by or administered to a subject in infant and/or child period.

The "infant and/or child period" of the invention refers to the period including "infant period and/or child period".

The "infant period" of the invention refers to the period from birth to before the age of 1 year (until the day before the day on which the subject turns 1 year old) when the subject is a human. The "infant period" refers to the period in which the subject takes milk such as breast milk as the major source of nutrient.

The "child period" of the invention refers to the period from the day on which the subject turns 1 year old to before entering later childhood when the subject is a human. The child period preferably refers to the period from the day on which the subject turns 1 year old to the day before earlier one of the day on which the subject turns 6 years old and the first day of elementary school, and may be the period from the day on which the subject turns 1 year old to the day before the day on which the subject turns 6 years old.

Accordingly, when the subject is a human, the composition of the invention is preferably taken or administered between birth and before becoming later childhood. In this regard, when the subject is a mammal other than human, the expression "later childhood" is replaced with the expression "growth period".

When the subject is a human, the composition of the invention is more preferably taken or administered between birth and before the age of 3 years (until the day before the day on which the subject turns 3 years old), further preferably taken or administered in infant period, still further preferably taken or administered between the age of three months and before the age of 1 year (until the day before the day on which the subject turns 1 year old).

When the subject is a mammal other than human, the periods are converted to the corresponding periods.

For example, the results of experiment using rats are shown in the Example described below.

The expression "infant period" used when the subject is a human corresponds to the period from birth to the age of 20 days in rats. Similarly, in cattle, the period corresponds to the period from birth to the day before the day on which the subject turns 10 weeks old. In goats, the period corresponds to the period from birth to the day before the day on which the subject turns 10 weeks old. In sheep, the period corresponds to the period from birth to the day before the day on which the subject turns 12 weeks old. In pigs, the period corresponds to the period from birth to the day before the day on which the subject turns 8 weeks old. In monkeys, the period corresponds to the period from birth to the day before the day on which the subject turns 14 weeks old. In dogs, the period corresponds to the period from birth to the day before the day on which the subject turns 6 weeks old. In cats, the period corresponds to the period from birth to the day before the day on which the subject turns 6 weeks old. In mice, the period corresponds to the period from birth to the age of 20 days. In hamsters, the period corresponds to the period from birth to the age of 20 days. In guinea pigs, the period corresponds to the period from birth to the age of 20 days.

The expression “child period” used when the subject is a human corresponds to the period from the age of 21 days to the day before the day on which the subject turns 5 weeks old in rats. Similarly, in cattle, the period corresponds to the period from the age of 10 weeks to the day before the day on which the subject turns 1 year old. In goats, the period corresponds to the period from the age of 10 weeks to the day before the day on which the subject turns 1 year old. In sheep, the period corresponds to the period from the age of 12 weeks to the day before the day on which the subject turns 1 year old. In pigs, the period corresponds to the period from the age of 8 weeks to the day before the day on which the subject turns 4 months old. In monkeys, the period corresponds to the period from the age of 14 weeks to the day before the day on which the subject turns 1.5 years old. In dogs, the period corresponds to the period from the age of 6 weeks to the day before the day on which the subject turns 6 months old. In cats, the period corresponds to the period from the age of 6 weeks to the day before the day on which the subject turns 6 months old. In mice, the period corresponds to the period from the age of 21 days to the day before the day on which the subject turns 5 weeks old. In hamsters, the period corresponds to the period from the age of 21 days to the day before the day on which the subject turns 5 weeks old. In guinea pigs, the period corresponds to the period from the age of 21 days to the day before the day on which the subject turns 5 weeks old.

The expression “3 years old” used when the subject is a human corresponds to 4 weeks old in rats. Similarly, in cattle, the age corresponds to 6 months old. In goats, the age corresponds to 6 months old. In sheep, the age corresponds to 6 months old. In pigs, the age corresponds to 3 months old. In monkeys, the age corresponds to 9 months old. In dogs, the age corresponds to 3 months old. In cats, the age corresponds to 3 months old. In mice, the age corresponds to 4 weeks old. In hamsters, the age corresponds to 4 weeks old. In guinea pigs, the age corresponds to 4 weeks old.

The expression “3 months old” used when the subject is a human corresponds to 5 days old in rats. Similarly, in cattle, the age corresponds to 2.5 weeks old. In goats, the age corresponds to 2.5 weeks old. In sheep, the age corresponds to 3 weeks old. In pigs, the age corresponds to 2 weeks old. In monkeys, the age corresponds to 3 weeks old. In dogs, the age corresponds to 1.5 weeks old. In cats, the age corresponds to 1.5 weeks old. In mice, the age corresponds to 5 days old. In hamsters, the age corresponds to 5 days old. In guinea pigs, the age corresponds to 5 days old.

The expression “1 year old” used when the subject is a human corresponds to 21 days old in rats. Similarly, in cattle, the age corresponds to 10 weeks old. In goats, the age corresponds to 10 weeks old. In sheep, the age corresponds to 12 weeks old. In pigs, the age corresponds to 8 weeks old. In monkeys, the age corresponds to 14 weeks old. In dogs, the age corresponds to 6 weeks old. In cats, the age corresponds to 6 weeks old. In mice, the age corresponds to 21 days old. In hamsters, the age corresponds to 21 days old. In guinea pigs, the age corresponds to 21 days old.

The composition of the invention has an action of improving the memory ability in later childhood of a subject who has taken or has been administered the composition in the infant and/or child period.

When the subject is a human, the expression “later childhood” of the invention refers to the period which is the earlier of the day on which the subject turns 6 years old and the first day of elementary school, to the later of the day on which the subject turns 12 years old and the last day of elementary school, and the expression “later childhood” may be the period from the day on which the subject turns 6 years old to the day on which the subject turns 12 years old. In this regard, when the subject is a mammal other than human, the expression “later childhood” is replaced with the expression “growth period”.

When the subject is a mammal other than human, the period is converted to the corresponding period.

For example, the results of experiment using rats are shown in the Example described below.

The expression “later childhood” used when the subject is a human corresponds to the period from the age of 5 weeks to the age of 8 weeks in rats. Similarly, in cattle, the period corresponds to the period from the age of 1 year to the age of 2 years. In goats, the period corresponds to the period from the age of 1 year to the age of 2 years. In sheep, the period corresponds to the period from the age of 1 year to the age of 2 years. In pigs, the period corresponds to the period from the age of 4 months to the age of 7 months. In monkeys, the period corresponds to the period from the age of 1.5 years to the age of 3 years. In dogs, the period corresponds to the period from the age of 6 months to the age of 1 year. In cats, the period corresponds to the period from the age of 6 months to the age of 1 year. In mice, the period corresponds to the period from the age of 5 weeks to the age of 8 weeks. In hamsters, the period corresponds to the period from the age of 5 weeks to the age of 8 weeks. In guinea pigs, the period corresponds to the period from the age of 5 weeks to the age of 8 weeks.

The memory ability of the invention includes working memory ability and the reference memory ability. In this regard, the working memory ability is sometimes referred to as working memory, spatial working memory ability, or short-term memory ability, and the working memory ability of the invention is the ability of comprehensive processing and short-term storing of information acquired with activities (spatial recognition, emotions, senses, and the like) and thus practicing the works more efficiently.

The reference memory ability is sometimes referred to as spatial reference memory ability or long-term memory ability.

Improvement of the working memory ability in later childhood can be evaluated, for example, with an eight-arm radial arm maze test as in the Example described below when the subject is a mammal such as a rat. It is a common technical knowledge in this field that memory ability can be evaluated with this test. Details are described, for example, in “Folia Pharmacologica Japonica, 130, 112 to 116 (2007)” or the like. In brief, when the memory ability is working memory ability, the ability can be evaluated by measuring the time required for an animal which has been on restricted feeding to collect the foods placed in all eight arms in an eight-arm radial arm maze or by measuring the number of re-entries to the arms which the animal has already entered. When the memory ability is reference memory ability, the ability can be evaluated with the number of correct entries to the arms with foods where the foods are placed in only four arms of an eight-arm radial arm maze.

When the subject is a human, the ability can be evaluated, for example, by Automated Working Memory Assessment (AWMA).

Because the working memory ability is a fundamental ability for learning, improvement of the working memory ability is expected to result in improvement of wide learning ability.

Examples of diseases, disorders, conditions, and symptoms (sometimes referred to as "diseases or the like" in this specification) which can be prevented or improved by improvement of the memory ability in later childhood include learning disorders (for example, dyslexia, dysgraphia, dyscalculia, geometric disorder, disorder of arithmetic skills, anomia and the like) and the like.

The amount of the bacterium of the invention present in the composition of the invention is appropriately set based on the form of the composition, but the total amount is preferably in the range of $1\times10^4$ to $1\times10^{13}$ cfu/g or $1\times10^4$ to $1\times10^{13}$ cfu/ml, more preferably in the range of $1\times10^5$ to $1\times10^{12}$ cfu/g or $1\times10^5$ to $1\times10^{12}$ cfu/ml, further preferably in the range of $1\times10^6$ to $1\times10^{10}$ cfu/g or $1\times10^6$ to $1\times10^{10}$ cfu/ml, further preferably in the range of $1\times10^6$ to $1\times10^9$ cfu/g or $1\times10^6$ to $1\times10^9$ cfu/ml.

In this specification, the "cfu" indicates the colony forming unit. Moreover, in this specification, when the bacterium of the invention is dead cells, cfu/g or cfu/ml can be replaced with cells/g or cells/ml.

The intake or the dosage of the composition of the invention is appropriately set based on the form of the composition, the usage, the subject, the age of the subject, the gender, the other conditions, and the like but is not particularly limited as long as an action of improving the memory ability in later childhood of a subject who has taken or has been administered the composition in the infant and/or child period is exhibited. The total amount of the bacterium of the invention per day per 100 g body weight is preferably in the range of $1\times10^4$ to $1\times10^{13}$ cfu, more preferably in the range of $1\times10^5$ to $1\times10^{12}$ cfu, further preferably in the range of $1\times10^6$ to $1\times10^{10}$ cfu, further preferably in the range of $1\times10^6$ to $1\times10^9$ cfu.

In this specification, when the bacterium of the invention is dead cells, cfu can be replaced with number of cells.

The composition of the invention can be taken or administered once a day or in separate portions. The composition may be taken or administered once over several days or over several weeks but is preferably administered every day. The administration period is preferably seven days or longer.

The composition of the invention can be taken or administered orally but is not limited thereto, and the composition may be, for example, taken or administered nasally or taken or administered through a gastric fistula or an intestinal fistula. For example, the composition may be taken by or administered to a subject through a nasogastric feeding tube or the like.

The composition of the invention can be used as a food or drink composition, a feed composition or a pharmaceutical composition.

For example, a food or drink composition for an infant and/or child for improving memory ability in later childhood, wherein the food or drink composition contains *Bifidobacterium longum* subsp. *infantis* as an active ingredient;

a feed composition for an infant and/or child for improving memory ability in growth period, wherein the feed composition contains *Bifidobacterium longum* subsp. *infantis* as an active ingredient; or a pharmaceutical composition for an infant and/or child for improving memory ability in later childhood, wherein the pharmaceutical composition contains *Bifidobacterium longum* subsp. *infantis* as an active ingredient can be provided.

The compositions are sometimes referred to as "the food or drink composition of the invention", "the feed composition of the invention" and "the pharmaceutical composition of the invention", respectively, below.

The food or drink composition of the invention is not particularly limited as long as the composition contains the bacterium of the invention. The food or drink composition is not limited regarding the form such as liquid, paste, gel solid, and powder, and may be a food or a drink, a tablet candy, a liquid food, or the like as well as the following examples: wheat products such as breads, macaroni, spaghetti, noodles, cake mixes, frying flours, and bread crumbs; instant foods such as instant noodles, cup noodles, retort-pouched/prepared foods, prepared canned foods, microwave foods, instant soups/stews, instant miso soups/clear Japanese soups, canned soups, freeze-dried foods, and other instant foods; processed agricultural products such as canned agricultural products, canned fruits, jams/marmalades, pickles, cooked beans, dried agricultural products, and cereals (processed grains); processed fishery products such as canned fishery products, fish hams/sausages, fishery paste products, fishery delicacies, and Tsukudani (foods boiled down in sweetened soy sauce); processed livestock products such as canned livestock products/pastes, and livestock hams/sausages; milk/dairy products such as processed milk, milk beverages, yogurts, lactic acid bacteria beverages, cheeses, ice creams, modified milk powders, creams, and other dairy products; oils and fats such as butter, margarine, and vegetable oils; basic condiments such as soy sauce, soybean paste, sauces, processed tomato condiments, Mirin (sweet sake for seasoning), and vinegars; compound flavor enhancers/foods such as cooking mixes, curry roux, sauces, dressings, noodle broths, spices, and other compound flavor enhancers; frozen foods such as frozen food materials, semi-cooked frozen foods, and cooked frozen foods; confectioneries such as caramels, candies, gummy candies, chewing gums, chocolates, cookies, biscuits, cakes, pies, snacks, crackers, Japanese-style confectioneries, rice confectioneries, bean confectioneries, desserts, jellies, and other confectioneries; luxury beverages such as carbonated drinks, natural juices, fruit juices, fruit juice-containing soft drinks, fruit flesh drinks, fruit granule-containing fruit juices, vegetable drinks, soy milk, soy milk drinks, coffee drinks, tea drinks, drink powders, concentrated drinks, sport drinks, nutritional drinks, alcohols, and other luxury beverages, other commercial foods and the like such as baby foods, Furikake (dry Japanese seasonings), and seasonings for Chazuke (boiled rice with hot tea); modified milk powder for infants and/or children; enteral nutrition products; food for special dietary uses, and food with health claims (foods for specified health uses, foods with nutrient function claims, and foods with function claims); nutritional supplements; and the like.

Moreover, the food or drink composition of the invention may be a supplement and may be, for example, a supplement in the tablet form. In the case of a supplement, the bacterium of the invention can be taken while the amount of meals and the calorie intake per day are not affected by other foods.

The food or drink composition of the invention can be produced by adding the bacterium of the invention to a general material of a food or a drink and can be produced in the same manner as that of a general food or drink except that the bacterium of the invention is added. The bacterium of the invention may be added in any stage of the production process of the food or drink composition. Moreover, the food or drink composition may be produced through a fermentation process by the added bacterium of the invention. Such food or drink compositions are lactic acid bacteria beverages, fermented milk, and the like. An embodiment of addition to pumped breast milk or modified milk is also included, and it is assumed that the milk after the addition is taken by an infant and/or child.

The food or drink composition of the invention also includes a material which is added to a food or drink composition during the production process of a food or drink composition or after the production, such as a material for producing a food or drink composition and a food additive. For example, the bacterium of the invention can be used as a starter for producing fermented milk. Moreover, the bacterium of the invention can be added later to produced fermented milk.

In the food or drink composition of the invention, a component which has a prebiotic effect which is known or will be found in the future or a component which supplements a prebiotic effect can be used as long as the effects of the invention are not impaired. For example, the food or drink composition of the invention can be produced by blending the bacterium of the invention with a component such as: various proteins such as whey protein, casein protein, soybean protein, and pea protein or mixtures or decomposition products thereof; amino acids such as leucine, valine, isoleucine, and glutamine; vitamins such as vitamin B6 and vitamin C; creatine; citric acid; fish oil; and oligosaccharides such as isomaltooligosaccharides, galactooligosaccharides, xylooligosaccharides, soybean oligosaccharides, fructooligosaccharides, and lactulose.

The amount of the bacterium of the invention present in the food or drink composition of the invention is appropriately set based on the form of the food or drink composition, but the total amount is preferably in the range of $1\times10^4$ to $1\times10^{13}$ cfu/g or $1\times10^4$ to $1\times10^{13}$ cfu/ml, more preferably in the range of $1\times10^5$ to $1\times10^{12}$ cfu/g or $1\times10^5$ to $1\times10^{12}$ cfu/ml, further preferably in the range of $1\times10^6$ to $1\times10^{10}$ cfu/g or $1\times10^6$ to $1\times10^{10}$ cfu/ml, still further preferably in the range of $1\times10^6$ to $1\times10^9$ cfu/g or $1\times10^6$ to $1\times10^9$ cfu/ml.

The intake of the food or drink composition of the invention is appropriately set based on the form of the food or drink composition, the usage, the subject, the age of the subject, the gender, the other conditions, and the like but is not particularly limited as long as an action of improving the memory ability in later childhood of a subject who has taken the food or drink composition in the infant and/or child period is exhibited. The total amount of the bacterium of the invention per day per 100 g body weight is preferably in the range of $1\times10^4$ to $1\times10^{13}$ cfu, more preferably in the range of $1\times10^5$ to $1\times10^{12}$ cfu, further preferably in the range of $1\times10^6$ to $1\times10^{10}$ cfu, further preferably in the range of $1\times10^6$ to $1\times10^9$ cfu.

In this regard, the food or drink composition of the invention can be taken once a day or in separate portions. The food or drink composition may be taken once in several days or in several weeks but is preferably administered every day. The administration period is preferably seven days or longer.

The food or drink composition of the invention may be taken alone or taken together with another food or drink composition, a food or a drink, a pharmaceutical composition, or a medicine. For example, the food or drink composition may be taken together with another food or drink composition for an infant and/or child, a food or a drink for an infant and/or child, a pharmaceutical composition for an infant and/or child, a medicine or the like for an infant and/or child for improving memory ability in later childhood.

The food or drink composition of the invention can be sold as a food or drink composition or a food or a drink with a label of use for an infant and/or child for improving the memory ability in later childhood after the growth or the like. In addition, of course, a term can be used as long as the term indicates a secondary effect caused by the use.

The "label" means all the acts for informing a consumer of the use, and all the labels which remind of/cause to guess the use are the "labels" of the invention, regardless of the purposes of the labels, the contents of the labels, the objects to be labeled, the media and the like. However, labeling with an expression which allows a consumer to directly recognize the use is preferable.

Specifically, examples are an act of describing the use on a product regarding the food or drink composition or the food or the drink of the invention or on packaging of a product, an act of transferring an article in which the use is described on a product or packaging of a product, delivering such an article, displaying such an article for transfer or delivery or importing such an article, an act of displaying or distributing an advertisement of a product, a price list or a business document with a description of the use thereon or providing information with such contents with a description of the use by an electromagnetic method (internet or the like) and other acts, and in particular, labeling on packaging, a container, a catalogue, a brochure, an advertisement material in a sales site such as POP, other documents, or the like is preferable.

The label is preferably a label approved by the administration or the like (for example, a label approved based on a system provided by the administration and provided in the form based on the approval). Examples include labels with food with health claims and the like, more specifically food with health claims, health foods, functional foods, enteral nutrition products, food for special dietary uses, foods with nutrient function claims, quasi-drugs or the like, and other examples include labels approved by the Consumer Affairs Agency, such as foods for specified health uses, foods with nutrient function claims, foods with function claims, and labels approved by a similar system. Examples of the latter include a label with foods for specified health uses, a label with qualified foods for specified health uses, a label indicating influence on the structure or the function of a body, a label with reduction of disease risk, a label with a scientifically grounded function, and the like. More specifically, examples include labels with food for specified health uses (especially labels with health uses) provided by the Cabinet Office Ordinance on Labeling Permission for Special Dietary Uses under the Health Promotion Act (Cabinet Office Ordinance No. 57 on Aug. 31, 2009), similar labels and the like.

An example of the food or drink composition of the invention when the subject is a human and when the subject takes the food or drink composition in the infant and/or child period is milk for infants (for example, modified milk powder for infants and the like) or milk for children (for example, modified milk powder for children and the like). In the invention, lactoferrin, a prebiotic such as human milk oligosaccharides, fructooligosaccharides and galactooligosaccharides, protein derived from casein, soybeans, whey or skimmed milk, a carbohydrate such as lactose, saccharose, maltodextrins, starch, and a mixture thereof, a lipid (for example, palmolein, sunflower oil or sunflower oil), a vitamin and a mineral which are essential in daily foods or the like can be contained, and one, two, or more kinds selected from the group can be contained. In particular, the "milk for infants" means a food which is designed in a way that an infant, preferably 4 to 12 months of age, more preferably 4 to 6 months of age, can drink as a breast milk substitute and which alone meets the nutritional demand of an infant.

Examples of the feed composition of the invention include pet food, livestock feed, fish farming feed and the like. The feed composition of the invention can be produced by mixing the bacterium of the invention to general feed or materials thereof such as grains, lees, bran, fish meal, bone meal, oils and fats, defatted milk powder, whey, mineral feed, and yeasts. The produced feed composition can be administered to general mammals, domestic animals, farmed fish, pets, and the like.

The amount of the bacterium of the invention present in the feed composition of the invention is appropriately set based on the form of the feed composition, but the total amount is preferably in the range of $1\times10^4$ to $1\times10^{13}$ cfu/g or $1\times10^4$ to $1\times10^{13}$ cfu/ml, more preferably in the range of $1\times10^5$ to $1\times10^{12}$ cfu/g or $1\times10^5$ to $1\times10^{12}$ cfu/ml, further preferably in the range of $1\times10^6$ to $1\times10^{10}$ cfu/g or $1\times10^6$ to $1\times10^{10}$ cfu/ml, further preferably in the range of $1\times10^6$ to $1\times10^9$ cfu/g or $1\times10^6$ to $1\times10^9$ cfu/ml.

The dosage of the feed composition of the invention to the subject is appropriately set based on the form of the feed composition, the usage, the subject, the age of the subject, the gender, the other conditions, and the like but is not particularly limited as long as an action of improving the memory ability in the growth period of a subject which has been administered with the feed composition in infant and/or child period is exhibited. The total amount of the bacterium of the invention per day per 100 g body weight is preferably in the range of $1\times10^4$ to $1\times10^{13}$ cfu, more preferably in the range of $1\times10^5$ to $1\times10^{12}$ cfu, further preferably in the range of $1\times10^6$ to $1\times10^{10}$ cfu, further preferably in the range of $1\times10^6$ to $1\times10^9$ cfu.

In this regard, the feed composition of the invention can be administered to the subject once a day or in separate portions. The feed composition may be administered once over several days or over several weeks but is preferably administered every day. The administration period is preferably seven days or longer.

The feed composition of the invention may be administered alone to the subject or administered together with another feed composition, feed, a pharmaceutical composition, or a medicine. For example, the feed composition may be administered together with another feed composition for an infant and/or child, feed for an infant and/or child, a pharmaceutical composition for an infant and/or child, a medicine for an infant and/or child, or the like for improving memory ability in growth period.

The pharmaceutical composition of the invention is not particularly limited as long as the bacterium of the invention is contained. As the pharmaceutical composition of the invention, the bacterium of the invention may be used directly or used after blending with a physiologically acceptable liquid or solid carrier for formulation and forming into a drug.

The dosage form of the pharmaceutical composition of the invention is not particularly limited, and specifically, examples include tablets, pills, powder, liquid preparation, suspensions, emulsions, granules, capsules, syrups, suppositories, injections, ointment, patches, eye drops, nasal drops, and the like. Moreover, for the formulation, an additive which is generally used as a carrier for formulation, such as excipients, binders, disintegrating agents, lubricants, stabilizers, flavoring agents, diluents, surfactants, and solvents for injection, can be used.

As the carrier for formulation, various organic or inorganic carriers can be used depending on the dosage form. Examples of the carrier in the case of solid preparation include excipients, binders, disintegrating agents, lubricants, stabilizers, flavoring agents, and the like.

Examples of the excipients include: saccharide derivatives such as lactose, sucrose, glucose, mannitol, and sorbitol; starch derivatives such as cornstarch, potato starch, α-starch, dextrin, and carboxymethyl starch; cellulose derivatives such as crystalline cellulose, hydroxypropyl cellulose, hydroxypropyl methylcellulose, carboxymethylcellulose, and carboxymethyl cellulose calcium; gum arabic; dextran; pullulan; silicate derivatives such as light silicic anhydride, synthetic aluminum silicate and magnesium aluminometasilicate; phosphate derivatives such as calcium phosphate; carbonate derivatives such as calcium carbonate; sulfate derivatives such as calcium sulfate; and the like.

Examples of the binders include, in addition to the excipients, gelatin, polyvinylpyrrolidone, macrogol and the like.

Examples of the disintegrating agents include, in addition to the excipients, chemically modified starch or cellulose derivatives such as croscarmellose sodium, sodium carboxymethyl starch and cross-linked polyvinylpyrrolidone, and the like.

Examples of the lubricants include: talc; stearic acid; metal stearates such as calcium stearate and magnesium stearate; colloidal silica; waxes such as Veegum and spermaceti wax; boric acid; glycols; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicic acid such as silicic anhydride and silicic acid hydrate; starch derivatives; and the like.

Examples of the stabilizers include: paraoxybenzoate esters such as methylparaben and propylparaben; alcohols such as chlorobutanol, benzyl alcohol, and phenylethyl alcohol; benzalkonium chloride; acetic anhydride; sorbic acid; and the like.

Examples of the flavoring agents include sweeteners, acidulants, aromas, and the like.

In this regard, the carriers used in the case of a liquid preparation for oral administration include solvents such as water, flavoring agents, and the like.

The amount of the bacterium of the invention present in the pharmaceutical composition of the invention is appropriately set based on the dosage form, the usage, the subject, the age of the subject, the gender, the type of disease or the like, the degree thereof, the other conditions, and the like, but the total amount is preferably in the range of $1\times10^4$ to $1\times10^{13}$ cfu/g or $1\times10^4$ to $1\times10^{13}$ cfu/ml, more preferably in the range of $1\times10^5$ to $1\times10^{12}$ cfu/g or $1\times10^5$ to $1\times10^{12}$ cfu/ml, further preferably in the range of $1\times10^6$ to $1\times10^{10}$ cfu/g or $1\times10^6$ to $1\times10^{10}$ cfu/ml, further preferably in the range of $1\times10^6$ to $1\times10^9$ cfu/g or $1\times10^6$ to $1\times10^9$ cfu/ml.

The dosage of the pharmaceutical composition of the invention to the subject is appropriately set based on the dosage form, the usage, the subject, the age of the subject, the gender, the type of disease, or the like, the degree thereof, the other conditions, and the like but is not particularly limited as long as an action of improving the memory ability in later childhood of a subject who has been administered the pharmaceutical composition in the infant and/or child period is exhibited. The total amount of the bacterium of the invention per day per 100 g body weight is preferably in the range of $1\times10^4$ to $1\times10^{13}$ cfu, more preferably in the range of $1\times10^5$ to $1\times10^{12}$ cfu, further preferably in the range of $1\times10^6$ to $1\times10^{10}$ cfu, further preferably in the range of $1\times10^6$ to $1\times10^9$ cfu.

The timing of administration of the pharmaceutical composition of the invention is not particularly limited as long as the timing is in the infant and/or child period of the subject, and the timing of administration can be appropriately chosen. The pharmaceutical composition may be administered prophylactically. Moreover, the form of administration is preferably determined based on the formulation form, the subject, the age of the subject, the gender, the type of disease or the like, the degree thereof, the other conditions, and the like. In this regard, in all the cases, the pharmaceutical composition of the invention can be administered once a day or in separate portions. The pharmaceutical composition may be administered once in several days or in several weeks but is preferably administered every day. The administration period is preferably seven days or longer.

The pharmaceutical composition of the invention may be administered alone or administered together with another pharmaceutical composition, a medicine, a food or drink composition, a food or a drink, a feed composition, or feed. For example, the pharmaceutical composition may be administered together with another pharmaceutical composition for an infant and/or child, a medicine for an infant and/or child, a food or drink composition for an infant and/or child, a food or a drink for an infant and/or child, a feed composition for an infant and/or child, feed for an infant and/or child or the like for improving memory ability in later childhood.

The invention can also include the following embodiments.

[1] Use of *Bifidobacterium longum* subsp. *infantis* in the manufacture of a composition for an infant and/or child for improving memory ability in later childhood.

[2] *Bifidobacterium longum* subsp. *infantis* for an infant and/or child for use in the improvement of memory ability in later childhood.

[3] A method for preventing or a method for improving a disease or the like which can be prevented or improved by improvement of memory ability in later childhood, including a step of administering *Bifidobacterium longum* subsp. *infantis* in an effective amount for the prevention or the improvement to an infant and/or child in need of the prevention or the improvement.

[4] Use of *Bifidobacterium longum* subsp. *infantis* for an infant and/or child for the improvement of memory ability in later childhood.

[5] *Bifidobacterium longum* subsp. *infantis* for an infant and/or child which is used for improving memory ability in later childhood.

[6] A method for preventing or a method for improving a disease or the like which can be prevented or improved by improvement of memory ability in later childhood, including a step of administering *Bifidobacterium longum* subsp. *infantis* or the composition of the invention to an infant and/or child.

[7] A method for improving memory ability in later childhood including a step of administering *Bifidobacterium longum* subsp. *infantis* to an infant and/or child; or a method for improving memory ability in later childhood of a subject including a step of administering *Bifidobacterium longum* subsp. *infantis* to the subject when the subject is an infant and/or child.

EXAMPLES

Although the invention is explained specifically below using an Example, the invention is not limited to the Example.

In the Example below, Sprague-Dawley (SD) rats (Tokyo Laboratory Animals Science Co., Ltd.) were used as test animals. The rats were kept in an animal room at room temperature (22±3° C.) on 12-hour light/dark cycle (light cycle at 7:00-19:00), and the animals were let freely eat (CE-2, CLEA Japan, Inc.) and drink water.

Example 1

Preparation of Test Animals

In this Example, 16-day-pregnant females (first pregnancy) (F0s) were kept in breeding cages (410 mm×260 mm) made of plastic from which the outside could not be seen, one animal in a cage, until neonates were born. After the birth, the neonates (F1s) were reduced at PND1, where the day of birth was considered as the postnatal day (PND) 0, in a manner that each litter included maximum 10 animals and included about the same numbers of males and females.

In this Example, only male F1s were used. Before the maternal separation (MS) treatment, the body weights were measured, and the animals were labeled with an animal marker (Muromachi Kikai Co., Ltd.). The MS treatment was conducted for three hours between 15 o'clock and 18 o'clock from PND5 to PND21.

The procedures of the MS treatment are as follows. An hour before starting the MS treatment, the home cages were moved to the laboratory (room temperature of 25° C.), and the animals were habituated to the environment. After moving the mothers from the home cages to other cages, the offspring (only the males were isolated) were moved from the home cages to individual cages (245 mm×160 mm) made of plastic and containing nothing, and the mothers were returned to the home cages. The individual cages were placed in a desiccator with five shelves made of acrylic resin (internal size of 430 mm×1330 mm×500 mm), and a heating pad was placed under the floor of each cage to keep the temperature of the cage at 25 to 27° C. The offspring which were not subjected to the MS treatment were kept with their mothers all the time.

(Eight-Arm Radial Arm Maze Test)

From PND5 to PND21, a solution of *Bifidobacterium longum* subsp. *infantis* NITE BP-02623 (Morinaga Milk Industry Co., Ltd.) suspended in physiological saline was orally administered to the test group as the test substance once a day at $5\times10^8$ CFU/100 g body weight (0.5 mL/100 g body weight as the solution), and a solution obtained by suspending an equivalent amount of ST starch (Nippon Starch Chemical Co., Ltd.) was orally administered to the control group as the control substance once a day. An eight-arm radial arm maze test was conducted using the rats of from PND42 (6 weeks old) to PND49 (7 weeks old).

In this test, a device composed of eight arms (55 cm×10 cm) and a central area (an octagon having a diameter of 30 cm) in which each arm was surrounded by transparent acrylic walls was used. Finely crushed foods (CE-2, CLEA Japan, Inc.) were placed at the ends of all the arms.

The animals were on restricted feeding for 45 minutes per day three days before the test, two days before the test and one day before the test. Moreover, habituation treatment in which the animals were put into the device and allowed to behave freely was also conducted one day before the test. The next day was counted as the initial day of the test (day 1 of the test), and the test was conducted once a day until day 6 of the test. The rats were moved to the test room and habituated one hour or more before conducting each session of the test. In the test, an animal was put in the central area of the device. The time required until the animal took all the foods placed at the ends of all the arms (the task completion time) was measured, and the number of errors which were the re-entries to the arms from which the foods had been already taken was counted at the same time. The behaviors of the animals were recorded on video.

The results are shown in FIGURE. The task completion time of the test group was lower than that of the control group on day 3 of the test and later. This suggests the improvement of the working memory ability by which the task could be practiced more efficiently.

The invention claimed is:

1. A method for improving memory ability in later childhood of a subject including administering a composition comprising a live *Bifidobacterium longum* subsp. *infantis* to the subject, and measuring improved memory ability in the subject in later childhood;

wherein said later childhood of a subject is a time period selected from the group consisting of:

a) when the subject is a human, between 6 and 12 years of age, b) when the subject is a rat, between 5 and 8 weeks of age, c) when the subject is a cow, between 1 and 2 years of age, d) when the subject is a goat, between 1 and 2 years of age, e) when the subject is a sheep, between 1 and 2 years of age, f) when the subject is a pig, between 4 and 7 months of age, g) when the subject is a monkey, between 1.5 and 3 years of age, h) when the subject is a dog, between 6 months and 1 year of age, i) when the subject is a cat, between 6 months and 1 year of age, j) when the subject is a mouse, between 5 and 8 weeks of age, k) when the subject is a hamster between 5 and 8 weeks of age, and l) when the subject is a guinea pig, between 5 and 8 weeks of age;

wherein said administering only occurs prior to the time period of later childhood;

wherein when the subject is a human, said subject experiences maternal separation prior to the time period of later childhood; and wherein when the subject is a rat, cow, goat, sheep, pig, monkey, dog, cat, mouse, hamster, or guinea pig, said subject experiences separation from the keeper prior to the time period of later childhood;

wherein the administered amount of said *Bifidobacterium longum* subsp. *infantis* is $1\times10^4$ to $1\times10^{13}$ cfu per day per 100 g body weight.

2. The method according to claim 1, wherein the *Bifidobacterium longum* subsp. *infantis* is *Bifidobacterium longum* subsp. *infantis* NITE BP-02623.

3. The method according to claim 1, wherein the memory ability is working memory ability.

4. A method for preventing or improving a disease, disorder, condition, or symptom which can be prevented or improved by improvement of memory ability in later childhood of a subject, including administering a composition comprising a live *Bifidobacterium longum* subsp. *infantis* in an effective amount for the prevention or the improvement to the subject in need of the prevention or the improvement, and measuring improved memory ability in the subject in later childhood;

wherein said later childhood of a subject is a time period selected from the group consisting of:

a) when the subject is a human, between 6 and 12 years of age, b) when the subject is a rat, between 5 and 8 weeks of age, c) when the subject is a cow, between 1 and 2 years of age, d) when the subject is a goat, between 1 and 2 years of age, e) when the subject is a sheep, between 1 and 2 years of age, f) when the subject is a pig, between 4 and 7 months of age, g) when the subject is a monkey, between 1.5 and 3 years of age, h) when the subject is a dog, between 6 months and 1 year of age, i) when the subject is a cat, between 6 months and 1 year of age, j) when the subject is a mouse, between 5 and 8 weeks of age, k) when the subject is a hamster between 5 and 8 weeks of age, and l) when the subject is a guinea pig, between 5 and 8 weeks of age;

wherein said administering only occurs prior to the time period of later childhood;

wherein when the subject is a human, said subject experiences maternal separation prior to the time period of later childhood; and wherein when the subject is a rat, cow, goat, sheep, pig, monkey, dog, cat, mouse, hamster, or guinea pig, said subject experiences separation from the keeper prior to the time period of later childhood;

wherein the administered amount of said *Bifidobacterium longum* subsp. *infantis* is $1\times10^4$ to $1\times10^{13}$ cfu per day per 100 g body weight.

5. The method according to claim 4, wherein the *Bifidobacterium longum* subsp. *infantis* is *Bifidobacterium longum* subsp. *infantis* NITE BP-02623.

6. The method according to claim 4, wherein the memory ability is working memory ability.

7. The method according to claim 4, wherein the disease, disorder, condition, or symptom is learning disorder.

8. The method according to claim 7, wherein the learning disorder is dyslexia, dysgraphia, dyscalculia, geometric disorder, disorder of arithmetic skills, or anomia.

9. The method of claim 1, wherein said composition consists of a live *Bifidobacterium longum* subsp. *infantis*.

10. The method of claim 4, wherein said composition consists of a live *Bifidobacterium longum* subsp. *infantis*.

11. The method of claim 1, wherein said composition is selected from the group consisting of a food, a drink, an animal feed, and a pharmaceutical.

12. The method of claim 4, wherein said composition is selected from the group consisting of a food, a drink, an animal feed, and a pharmaceutical.

13. The method of claim 1, wherein the period of said maternal separation or separation from the keeper is three hours or longer per a day.

14. The method of claim 4, wherein the period of said maternal separation or separation from the keeper is three hours or longer per a day.

15. The method of claim 1, wherein said subject is male.

16. The method of claim 4, wherein said subject is male.

* * * * *